United States Patent [19]

Ricciardelli et al.

[11] Patent Number: 4,592,368

[45] Date of Patent: Jun. 3, 1986

[54] GAS ANALYZER PROTECTION SYSTEM

[75] Inventors: Robert H. Ricciardelli, Waukesha; Robert M. Sommer, Colgate, both of Wis.

[73] Assignee: Biochem International Inc., Waukesha, Wis.

[21] Appl. No.: 540,803

[22] Filed: Oct. 11, 1983

[51] Int. Cl.$^4$ ............................................. A61B 5/08
[52] U.S. Cl. ......................................... 128/719; 128/730; 128/205.27; 55/215
[58] Field of Search .............. 128/719, 730, 718, 716, 128/205.27; 55/213, 163, 215; 73/863.21

[56] References Cited

U.S. PATENT DOCUMENTS

| | | | |
|---|---|---|---|
| 2,195,898 | 4/1940 | Newton | 183/2.5 |
| 3,236,188 | 2/1966 | Eves et al. | 103/150 |
| 3,243,941 | 4/1966 | Peterson | 55/204 |
| 3,692,437 | 9/1972 | Ray | 417/533 |
| 3,802,417 | 4/1974 | Lang | 128/716 |
| 3,895,927 | 7/1975 | Bournham | 55/170 |
| 4,018,579 | 4/1977 | Hofmann | 55/213 |
| 4,026,685 | 5/1977 | Grix | 55/213 |
| 4,047,909 | 9/1977 | Hofmann | 55/213 X |
| 4,182,136 | 1/1980 | Morse | 62/503 |
| 4,197,858 | 4/1980 | Osborn | 128/718 |
| 4,304,578 | 12/1981 | Hakala et al. | 55/189 |
| 4,335,574 | 6/1982 | Sato et al. | 55/213 X |
| 4,413,632 | 11/1983 | Schlessinger et al. | 128/716 |
| 4,446,869 | 5/1984 | Knodle | 128/719 X |
| 4,475,932 | 10/1984 | Hull et al. | 55/170 |
| 4,476,708 | 10/1984 | Baker et al. | 73/23 |
| 4,483,697 | 11/1984 | Deysson et al. | 55/205 |

Primary Examiner—Kyle L. Howell
Assistant Examiner—John C. Hanley
Attorney, Agent, or Firm—Willian Brinks Olds Hofer Gilson & Lione Ltd.

[57] ABSTRACT

A protection system for a gas analyzer is described which monitors gas pressure adjacent a sample cell included in the analyzer. The sample cell is connected via a gas/liquid separator to an input sample conduit. The measured pressure indicates when the separator is clogged with excessive liquid. A control circuit is provided which responds to selected pressure conditions by automatically controlling the valve to interrupt the flow of gas from the separator to the sample chamber. In this way, the sample chamber is protected against contamination by liquid. In the preferred embodiment, the sample chamber and the separator are automatically backflushed to remove any water contamination.

11 Claims, 4 Drawing Figures

4,592,368

GAS ANALYZER PROTECTION SYSTEM

BACKGROUND OF THE INVENTION

The present invention relates to a protection system for use with a gas analyzer of the type used to analyze gases exhaled by a patient.

In the past, gas analyzers have been used to monitor the composition of gases exhaled by a patient. For example, $CO_2$ concentration can be used to monitor the physiology of a patient, as for example during a surgical procedure. It has been recognized for some time that a gas/liquid separator is needed to remove liquids exhaled by the patient to prevent these liquids from entering the gas analyzer. U.S. Pat. No. 4,304,578 to Hakala et al discloses one such prior art water separator for a gas analyzer.

However, this separator of the prior art is not without its disadvantages. In particular, when the water content of the fluid entering the separator exceeds the capacity of the separator, the separator can pass liquid to the gas analyzer. When this happens, optical components of the gas analyzer can be fouled, thereby interrupting the operation of the gas analyzer. Typically, when liquid enters the gas analyzer the analyzer must be taken off line and cleaned before it is again capable of providing reliable measurements of gas content.

SUMMARY OF THE INVENTION

The present invention is directed to a protection system for a gas analyzer which automatically responds to blockage of a separator so as to reduce or eliminate the passage of liquid from the separator into the gas analyzer.

The present invention is intended for use with a gas analyzer of the type which comprises a sample cell, a gas/liquid separator, a sample tube for conducting a gas/liquid mixture from a patient to the separator, and means for moving gas from the separator through the sample chamber. The protection system of this invention comprises sensor means for measuring pressure in the moving means and for generating a pressure signal in response thereto. Valve means are provided for selectively permitting and interrupting the flow of gas from the separator to the sample chamber. A control means is provided which is responsive to the pressure signal and operates automatically to control the valve means to interrupt the flow of gas from the separator to the sample chamber when the pressure signal enters a selected range of values indicative of excessive liquid in the separator. In the preferred embodiment described below, the protection system operates automatically to backflush the sample cell and the gas/liquid separator when the valve means is controlled to interrupt flow of gas from the separator to the sample chamber. In this way, the separator can be rapidly cleared of excessive liquid and the interruption in analyzing time can be minimized.

This invention provides the important advantage that it automatically reacts to the presence of excessive liquid in the gas/liquid separator or the sample tube and prevents liquid from passing through the separator into the sample cell. In this way contamination of the sample cell is minimized, along with associated interruptions in the operation of the analyzer. Once the separator has been cleared of excessive liquid, the preferred embodiment described below operates automatically to restore the analyzer to normal operation.

The invention itself, together with further objects and attendant advantages, will best be understood by reference to the following detailed description, taken in conjunction with the accompanying drawings.

DETAILED DESCRIPTION OF THE PRESENTLY PREFERRED EMBODIMENTS

Figure 1:
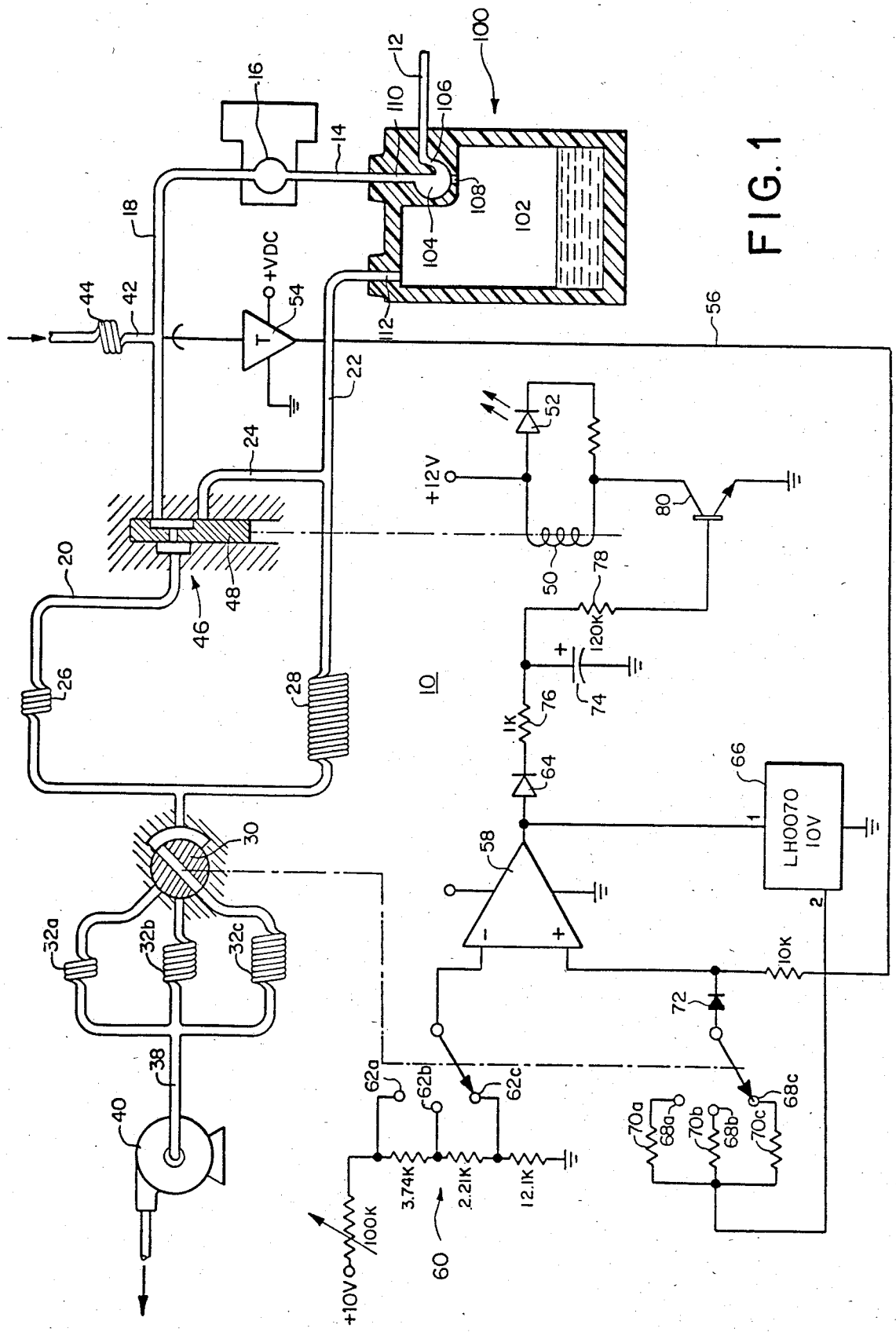
FIG. 1 is a schematic diagram of portions of a gas analyzer which incorporates a presently preferred embodiment of this invention.

Turning now to the drawings, FIG. 1 shows a schematic view of portions of a gas analyzer 10 which incorporates the presently preferred embodiment of this invention. As shown in FIG. 1, this gas analyzer 10 includes a sample input conduit 12 which is coupled to a gas/liquid separator 100. The input conduit 12 serves to pass a sample from a patient to the separator 100. In this preferred embodiment, the input conduit 12 is 5 feet in length, is formed of a flexible plastic material, and is provided with an inside diameter of 0.040 inches.

The gas analyzer 10 also includes a sample chamber 16 which is connected to the separator 100 by a conduit 14. The analyzer 10 includes means (not shown) for analyzing the $CO_2$ content of gas in the sample chamber 16. The details of the structure of this portion of the analyzer 10 do not per se form part of this invention, and are not therefore described in detail here. A wide variety of infrared absorption systems can be used to detect $CO_2$ optically, such as the systems used in the gas analyzers marketed by Puritan Bennett or Biochem International Inc.

Gas which passes out of the sample chamber 16 passes via a conduit 18 to a valve 46 which will be described in greater detail below. Gas flows from the valve 46 via a conduit 20 and a flow restrictor 26 to a flow selector 30. The flow selector 30 has three positions and operates to direct the gas from the restrictor 26 to one of the three flow restrictors 32a, 32b, 32c. These three flow restrictors 32a, 32b, 32c are connected in parallel to a conduit 38 which is in turn connected to a vacuum pump 40. In addition, the flow selector 30 receives gas directly from the separator 100 via the conduit 22 and the flow restrictor 28. A conduit 24 is provided interconnecting the conduit 22 and the valve 46. In addition, a vent conduit 42 is connected to the conduit 18 by means of yet another flow restrictor 44.

In this preferred embodiment, each of the flow restrictors 26, 28, 32a, 32b, 32c and 44 is formed of an appropriate length of tubing of 0.010 inches in internal diameter. The three flow restrictors 32a, 32b and 32c are provided with a length appropriate to cause the gas flow through the flow selector 30 to equal 150 cc per minute when the restrictor 32a is selected, 75 cc per minute when the restrictor 32b is selected, and 25 cc per minute when the restrictor 32c is selected. In this embodiment the restrictor 28 is 6 feet in length and the restrictor 26 is 2 inches in length such that the fluid flow through the conduit 20 is about 14 times the fluid flow through the conduit 22. In this embodiment, the restrictor 44 is 3 feet in length.

The valve 46 is a solenoid valve which is controlled by current through a coil 50. Depending on the presence or absence of current in the coil 50, a valve member 48 included in the solenoid valve 46 is positioned to block either the conduit 24 or the conduit 18. In this embodiment, the solenoid valve 46 operates to block the conduit 24 in the absence of current through the coil 50. Merely by way of example, the solenoid valve 46 can be of the type marketed by Clippard as Model No. EVO 3. An LED 52 is connected in parallel with the coil 50 to provide a visual indication of when the solenoid valve 46 is energized to block the conduit 18 and provide an interconnection between the conduit 24 and the conduit 20.

The embodiment of FIG. 1 includes a pressure transducer or sensor 54 which operates to generate an electrical signal on line 56 which is indicative of the pressure of the fluid in the conduit 18. Purely by way of example, in this embodiment the transducer 54 is of the type distributed by Microswitch as Model No. 141PC06D. This transducer 54 produces a voltage on line 56 which varies in inverse proportion to the pressure in the conduit 18. Thus, the lower the pressure in the conduit 18, the higher the voltage on line 56. The voltage on line 56 is in effect a pressure signal which is applied to the noninverting input of a comparator 58. The inverting input of the comparator 58 is connected to one of three terminals 62a, 62b, 62c of a voltage divider 60. Thus, one of three reference voltages is applied to the comparator 58 by the voltage divider 60, in accordance with which of the terminals 62a,62b,62c is utilized. The output of the comparator 58 is applied as an input to a voltage regulator 66. This voltage regulator 66 operates to generate a 10 volt output voltage whenever the output of the comparator 58 is high. The output voltage of the voltage regulator 66 is applied in parallel to three resistors 70a,70b,70c. Three terminals 68a,68b,68c are provided, each connected to a respective aone of the resistors 70a,70b,70c. Any one of these three terminals 68a,68b,68c can be connected via a diode 72 to the noninverting input of the comparator 58.

In this embodiment, the three restrictors 32a,32b,32c, the three terminals 62a,62b,62c and the three terminals 68a,68b,68c are switched in a coordinated manner. For example, when the flow restrictor 32a is selected to provide a 150 cc per minute flow rate through the flow selector 30, the terminal 62a is selected to provide an appropriate reference voltage for the comparator 58, and the terminal 68a is selected to provide an appropriate hysteresis voltage for the comparator 58. Thus, when the flow selector 30 is used to choose any one of the three restrictors 32a,32b,32c in accordance with the desired fluid flow rate, both the threshhold voltage to the comparator 58 and the hysteresis voltage to the comparator 58 are automatically adjusted to the appropriate value.

The output signal of the comparator 58 also charges a capacitor 74 via a diode 64 and a resistor 76. Once the capacitor 74 is charged, current passes via the resistor 78 to turn on the transistor 80, thereby energizing the coil 50 and switching the solenoid valve 46 to block flow through the conduit 18. In this embodiment, the resistor 76 is a 1K resistor, and the resistor 78 is a 120K resistor. This choice of resistances causes the capacitor 76 to charge quickly but to discharge slowly through the transistor 80. In this way, the transistor 80 is maintained in the conducting condition for approximately 1 second after the output of the comparator 58 falls to the low state. Simply by way of example, the transistor 80 can be of the type 2N3417, the comparator 58 can be type LM358, and the voltage regulator 66 can be type LH0070.

Figure 2:
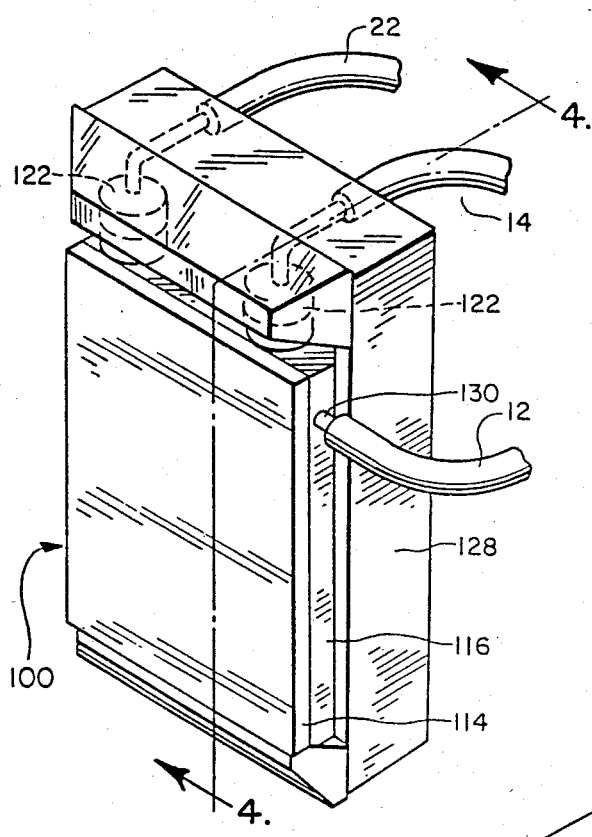
FIG. 2 is a perspective view showing the gas/liquid separator mounted in the analyzer of FIG. 1.
Figure 4:
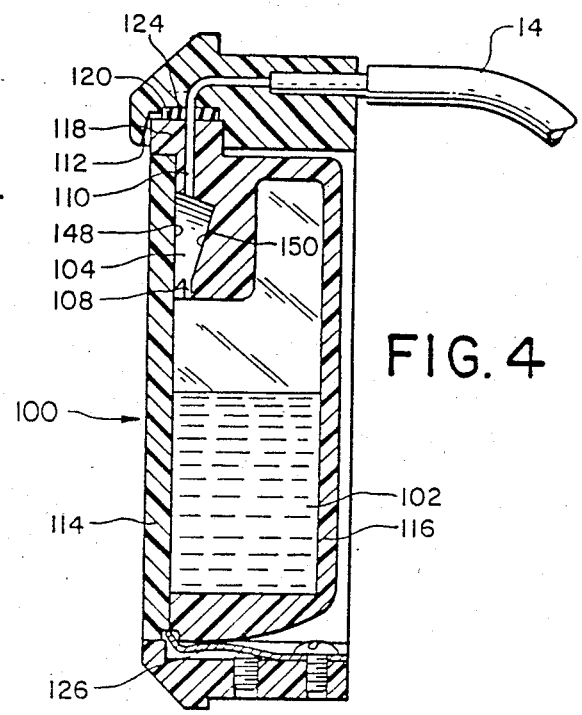
FIG. 4 is a sectional view taken along line 4—4 of FIG. 2.
Figure 3:
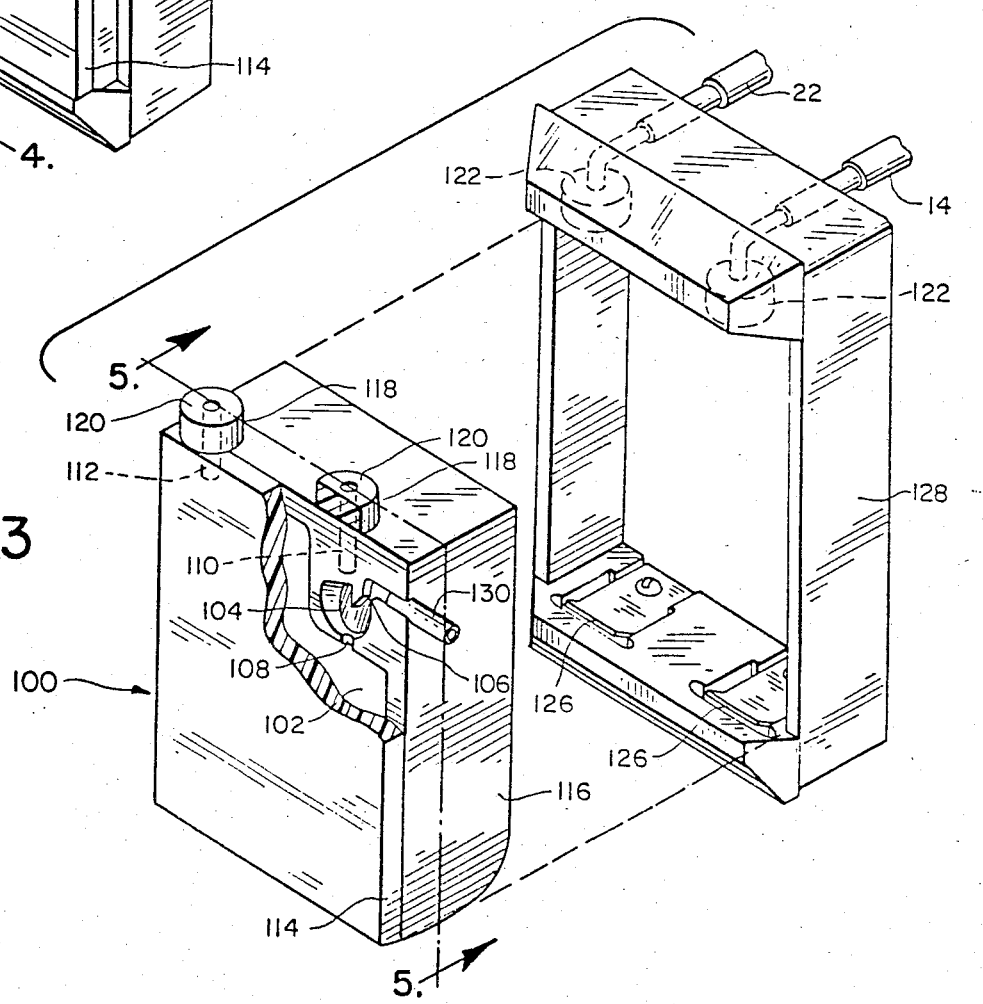
FIG. 3 is an exploded view of the structure of FIG. 2 in partial cutaway.

Turning now to FIGS. 2–4, the separator 100 does not form part of this invention. It is claimed in a copending application assigned to the assignee of this invention. Merely for completeness, it will be described here. The separator is a single, integral unit which defines both a collection chamber 102 and a separator chamber 104. The separator chamber 104 is provided with an input port 106, a lower output port 108, and an upper output port 110. The collection chamber 102 is provided with a suction port 112. As best seen in FIG. 2, the input port 106 is connected to the sample input conduit 12 to receive the fluid sample from a patient. The lower output port 108 is defined at the lowermost portion of the separator chamber 104 and serves to interconnect the separator chamber 104 and the collection chamber 102. The upper output port 110 is situated at the uppermost portion of the separator chamber 104 and is connected to the conduit 14 to supply gas to the sample chamber 16. The suction port 112 is connected via the conduit 22 to the restrictor 28 and the flow selector 30.

The separator 100 is formed of two pieces of suitable plastic, such as Plexiglas: a body 116 and a cover plate 114. The body 116 defines the collection chamber 102, the separator chamber 104 and the ports 106,108,110,112. The cover plate 114 is a flat plastic plate which is securely bonded to the body 116 to enclose the collection chamber 102 and the separator chamber 104. Any suitable bonding technique can be used to join the body 116 and the cover plate 114. Epoxy cements, solvent-type cements, or ultrasonic welding techniques can be used. Whatever the method used, the junction between the body 116 and the cover plate 114 should be leakproof and secure in the presence of water and 100% humidity.

As shown in FIG. 3, the body 116 defines two sealing lugs 118 around the upper output port 110 and the suction port 112. Each of these lugs 118 defines a respective sealing surface 120.

The separator 100 is sized to fit within a receiving well 128 in the analyzer 10. This receiving well 128 defines two spaced wells 122 sized to receive the lugs 118. Each of the wells 122 includes a respective gasket 124 which operates to generate a gas-tight seal against the sealing surface 120 of the respective lug 118. The wells 122 serve to interconnect the conduits 14,22 with the upper output port 110 and suction port 112, respectively. Springs 126 are provided at the lower portion of the receiving well 128 to bias the separator 100 upwardly in order to ensure a firm, air-tight seal between the gaskets 124 and the sealing surfaces 120. A metal tube 130 extends out of the input port 106 and serves to interconnect the input port 106 with the input conduit 12.

OPERATION

In operation, the embodiment described above provides important advantages in terms of effective gas/water separation and effective protection for the sample chamber 16 against contamination by liquid.

When the coil 50 is not energized, the solenoid valve 46 allows gas to pass directly from the conduit 18 to the conduit 20 and blocks the conduit 24. Thus, in the normal mode of operation, a sample passes via the input conduit 12 to the separator chamber 104. The liquid portion of the sample passes to the collection chamber 102 and the gas portion of the sample passes via the conduit 14 to and through the sample chamber 16. Gas which has flowed through the sample chamber 16 passes through the conduits 18, 20 and 38 to the vacuum pump 40. The pump 40 also operates to draw a lesser flow through the collection chamber 102 and the conduit 22 in order to extract liquid efficiently from the separator chamber 104. In the preferred embodiment, this lesser flow through the suction port 112 is in the range of 2–10% of the flow rate through the sample port 110. During this normal mode of operation, the transducer 54 generates a relatively low pressure signal on line 56, less than the reference voltage applied to the inverting input of the comparator 58. For this reason, the output signal of the comparator 58 is low and no current flows through the diode 72 or to the base of the transistor 80. The transistor 80 is in a nonconducting state and no current is passed through the coil 50.

In the event excessive liquid is present in the input conduit 12 or the separator chamber 104, the gas pressure in the conduits 14,18 will fall. This will cause the pressure signal on line 56 to increase. At the point where the pressure signal on line 56 exceeds the reference voltage applied to the inverting input of the comparator 58, the output of the comparator 58 will go high, thereby charging the capacitor 74 an causing the transistor 80 to conduct. In this way the coil 50 is energized and the solenoid valve 46 is controlled to block the conduit 18 and to allow gas to flow from the conduit 24 directly to the conduit 20.

When the solenoid valve 46 has switched to this energized state, flow from the separator chamber 104 to the sample chamber 16 is terminated. This is because suction is no longer being applied to the conduit 18. Simultaneously, increased flow rates are drawn through the conduits 22,24. In this way, the flow rate through the collection chamber 102 is increased and air is drawn via the vent conduit 42 and the conduits 18 and 14 through the sample chamber 16 and the separator chamber 104 into the collection chamber 102. This backflushing of the sample cell 16, the conduits 14,18 and the separator chamber 104 serves to clear these elements of any accumulated liquid.

Furthermore, when the output of the comparator 58 goes high the voltage regulator 66 is caused to apply a 10-volt signal to the resistors 70a,70b,70c. The selected one of the resistors 70a,70b,70c provides a voltage via the diode 72 to the noninverting input of the comparator 58. This voltage is in effect added to the pressure signal on line 56 and ensures that the output of the comparator 58 remains high until the pressure signal on line 56 has fallen to a suitably low value. Thus, the voltage regulator 66 and the resistors 70a,70b,70c cooperate to provide a desired degree of hysteresis to the circuit. When the pressure signal reaches a suitably low value (indicative of a suitably high pressure in the conduit 18) the output of the comparators 58 goes low, thereby deenergizing the coil 50 and causing the solenoid valve 46 to return to its normal state in which the conduit 18 is interconnected with the conduit 20 and the conduit 24 is blocked.

The resistors included in the voltage divider 60 and the resistors 70a,70b,70c should be selected for the particular application to provide the desired switching points for the comparator 58. For any given flow rate and sample input conduit 12, the voltage divider 60 should be selected such that the coil 50 is energized at the point where liquid water begins moving along the inner walls of the sample input conduit 12. Similarly, the resistors 70a,70b,70c should be selected such that the coil 50 is deenergized when the pressure in the conduit 18 rises to a value indicative of the presence of water droplets on the sample input conduit 12, which water droplets are, however, not so large as to move with the air flow.

From the foregoing, it should be apparent that the preferred embodiment described above provides important advantages. In particular, the protection system operates automatically to prevent the contamination of the sample chamber 16 by liquid and to backflush the system in order to clear a clogged separator chamber automatically and quickly. All of this is accomplished in a simple, automatic manner without operator intervention to reduce interruptions in the operation of the gas monitor 10 caused by liquid contamination of the sample chamber 16.

Yet another advantage of the protection system of this invention is that the flow through the sample input conduit 12 is not interrupted when the coil 50 is energized. Rather, the flow through the input conduit 12 passes into the collection chamber 102 rather than to the sample cell 16. By maintaining the flow in the input conduit 12, the present invention ensures that reliable measurements can be resumed as soon as the blockage in the separator chamber 104 is cleared.

Of course, it should be understood that a wide range of changes and modifications to the preferred embodiment described above will be apparent to those skilled in the art. For example, the protection system described above can be used with other types of separators 100 or analyzers 10. In addition, dimensions and materials can be modified as desired to suit the intended application. It is therefore intended that the foregoing detailed description be regarded as illustrative rather than limiting, and that it be understood that it is the following claims, including all equivalents, which are intended to define the scope of this invention.

We claim:

1. In a gas analyzer of the type comprising a sample cell, a gas/liquid separator including an outlet port and an inlet port, a sample tube for conducting a gas/liquid mixture from a patient to the separator input port, and means for conducting gas from the separator output port through the sample chamber, the improvement comprising:

sensor means for measuring pressure in the conducting means and for generating a pressure signal in response thereto;

valve means for selectively permitting and interrupting flow of gas from the separator to the sample chamber; and control means, responsive to the pressure signal, for automatically controlling the valve means to interrupt flow of gas from the separator to the sample chamber when the pressure signal enters a selected range of values indicative of excessive liquid in the separator.

2. The invention of claim 1 wherein the conducting means includes a vacuum pump operative to draw gas from the separator through the sample chamber, and wherein the selected range of values is indicative of excessively low pressure in the conducting means.

3. The invention of claim 2 further comprising: a vent in said means for conducting positioned between said valve means and said sample cell.

4. The invention of claim 3 wherein the separator further includes a suction port and wherein the valve means causes gas to flow from the sample chamber to the separator and out the suction port when the flow of gas from the separator to the sample chamber is interrupted in order to clear the separator of liquid.

5. In a gas analyzer of the type comprising a sample cell, a gas/liquid separator having an input port, an output port, and a suction port, a sample tube for conducting a gas/liquid mixture from a patient to the input port, and a suction system for applying suction to the suction port and for drawing gas from the output port through the sample cell, to a suction pump, the improvement comprising:
  a valve means included in the suction system, said valve means having a first port connected to the suction pump, a second port connected to the sample cell, and third port connected to the suction port, said valve means operating to pass fluid from the second port to the first port when the valve means is in a normal state and to pass fluid from the third port to the first port when the valve means is in a switched state;
  pressure transducer means for generating a pressure signal indicative of the pressure of gas flowing through the sample cell at a point between the valve means and the separator; and
  control means, responsive to the pressure signal, for controlling the valve means such that the valve means is in the normal state when the pressure signal is in a first range of values indicative of normal separator operation, thereby passing fluid from the sample cell to the suction pump, and the valve means is in the switched state when the pressure signal is in a second range of value indicative of excessively low pressure, thereby passing fluid from the suction port to the suction pump.

6. The invention of claim 5 further comprising:
  a vent line positioned between the sample cell and the valve means to provide a flow of gas through the sample cell and the separator when the valve means is in the switched state.

7. The invention of claim 5 wherein the first and second ranges of values overlap such that the control means switches the valve means to the switched state at a lower pressure than that at which the control means switches the valve means to the normal state.

8. The invention of claim 5 wherein the suction system comprises means for setting the flow rate through the suction port to be in the range of 2–10% of the flow rate through the output port when the valve means is in the normal position.

9. In a gas analyzer of the type comprising a sample cell, a gas/liquid separator including suction and outlet ports and an inlet port, a sample tube for conducting a gas/liquid mixture from a patient to the separator inlet, and means for conducting gas from the separator outlet port through the sample cell, the improvement comprising:
  a suction pump included in the conducting means;
  at least one conduit included in the conducting means, said conduit connecting the separator outlet port and sample cell to the suction pump;
  a valve positioned in said conduit between the suction pump and the separator;
  pressure sensor means for measuring the fluid pressure in said conduit at a point between the valve and the separator and generating a signal in response thereto;
  controller means, responsive to the signal, for controlling the valve such that the valve allows the suction pump to draw flow from the outlet port through the sample cell when the signal is in a first range of values indicative of normal operations and the valve switches to suspend flow from the outlet port to the sample cell when the signal is in a second range of values indicative of excessive liquid in the separator.

10. The invention of claim 9 further comprising: a vent in said means for conducting positioned between said valve and said sample cell.

11. The invention of claim 10 further comprising:
  a conduit connecting the separator suction port to the suction pump.

* * * * *